United States Patent
Ikonen et al.

(10) Patent No.: US 10,375,551 B2
(45) Date of Patent: Aug. 6, 2019

(54) WIRELESS MEDICAL BODY AREA NETWORK AND METHOD TO ASSOCIATE WIRELESS DEVICES THEREWITH

(71) Applicant: GENERAL ELECTRIC COMPANY, Schenectady, NY (US)

(72) Inventors: Emma Elina Ikonen, Helsinki (FI); Kristian Matti Karru, Helsinki (FI); Otto Valtteri Pekander, Helsinki (FI)

(73) Assignee: General Electric Company, Schenectady, NY (US)

(*) Notice: Subject to any disclaimer, the term of this patent is extended or adjusted under 35 U.S.C. 154(b) by 10 days.

(21) Appl. No.: 15/540,919

(22) PCT Filed: Sep. 18, 2015

(86) PCT No.: PCT/US2015/050875
§ 371 (c)(1),
(2) Date: Jun. 29, 2017

(87) PCT Pub. No.: WO2016/108967
PCT Pub. Date: Jul. 7, 2016

(65) Prior Publication Data
US 2017/0347254 A1 Nov. 30, 2017

(30) Foreign Application Priority Data
Dec. 30, 2014 (GB) .................................. 1423330.8

(51) Int. Cl.
*H04W 8/00* (2009.01)
*H04W 4/80* (2018.01)
(Continued)

(52) U.S. Cl.
CPC ............ *H04W 4/80* (2018.02); *A61B 5/0024* (2013.01); *H04B 13/005* (2013.01); *H04W 4/08* (2013.01);
(Continued)

(58) Field of Classification Search
CPC ......... H04W 8/005; H04W 4/21; H04W 4/80; H04W 4/206; H04W 4/008; H04B 13/005; A61B 5/0024
See application file for complete search history.

(56) References Cited

U.S. PATENT DOCUMENTS 8,918,854 B1 * 12/2014 Giobbi ............... G06K 7/10366
726/9
9,031,543 B2 * 5/2015 Lee ..................... H04L 12/1804
455/416
(Continued)

FOREIGN PATENT DOCUMENTS

EP 2020784 A1 2/2009
WO 2012107866 A1 8/2012

OTHER PUBLICATIONS

Li et al., "Group Device Pairing based Secure Sensor Association and Key Management for Body Area Networks," IEEE INFOCOM 2010 Proceeding, IEEE, Mar. 14, 2010, 10 pages (Year: 2010).*
(Continued)

*Primary Examiner* — Lan-Huong Truong

(57) ABSTRACT

A method of associating wireless devices with a wireless medical body area network, MBAN, where the wireless MBAN comprises at least one host is provided. The method comprises activating the host to search for wireless devices in range; displaying a list on the host of available wireless devices in range, wherein displaying the list comprises displaying each wireless device on the list with a unique representation on the list and the same unique representation on the wireless device itself; selecting a wireless device on the list; and associating the selected wireless device on the list with the host.

16 Claims, 4 Drawing Sheets

(51) Int. Cl.
*H04W 4/38* (2018.01)
*H04W 4/08* (2009.01)
*A61B 5/00* (2006.01)
*H04W 4/21* (2018.01)
*H04B 13/00* (2006.01)

(52) U.S. Cl.
CPC .............. *H04W 4/21* (2018.02); *H04W 4/38* (2018.02); *H04W 8/005* (2013.01)

(56) References Cited

U.S. PATENT DOCUMENTS

| | | | |
|---|---|---|---|
| 9,154,303 B1* | 10/2015 | Saylor | H04L 63/08 |
| 2008/0009309 A1* | 1/2008 | Gha | H04M 1/7253 455/550.1 |
| 2011/0305376 A1* | 12/2011 | Neff | G16H 40/20 382/128 |
| 2012/0017242 A1* | 1/2012 | Newell | H04N 21/2743 725/38 |
| 2012/0242501 A1* | 9/2012 | Tran | A61B 5/0024 340/870.02 |
| 2013/0045764 A1 | 2/2013 | Vik et al. | |
| 2013/0046871 A1* | 2/2013 | Vik | H04W 4/023 709/223 |
| 2013/0337749 A1* | 12/2013 | Wang | H04W 4/80 455/41.2 |
| 2014/0108606 A1* | 4/2014 | Beadles | G06F 17/30876 709/217 |
| 2014/0343967 A1* | 11/2014 | Baker | G16H 10/65 705/3 |
| 2015/0164323 A1* | 6/2015 | Holtzclaw | A61B 5/0022 600/365 |

OTHER PUBLICATIONS

International Search Report and Written Opinion for PCT/US2015/050875, dated Nov. 25, 2015, 14 pages.
Combined Search and Exam Report for corresponding GB Appln. No. 1423330.8, dated Jun. 19, 2015, 5 pages.
Washington et al., "Federal Comminications Commission FCC 12-54 Before the Federal Comminications Comnission 96, Appendix A—Commenting Parties, Appendix B—Final Rules, Appendix C—Final Regulatory Flexibility Analysis," Retrieved from Internet: https://apps.fcc.gov/edocs_public/attachmatch/FCC-12-54A1, May 24, 2012, Retrieved on Nov. 16, 2015, (No Longer available) 1 page.
"IEEE Standard for Local and metropolitan area networks—Part 15.6: Wireless Body Area Networks," IEEE Computer Society, Std 802.15.6-2012, IEEE Standard, Feb. 29, 2012, 271 pages.
Harbert, "FCC Gives Medical Body Area Networks Clean Bill of Health—IEEE Spectrum," Retrieved from Internet: http://spectrum.ieee.org/tech-talk/biomedical/devices/fcc-gives-medical-body-area-netowrks-clean-bill-of-health, Jun. 4, 2012, Retrieved on Nov. 13, 2015, 2 pages.
Wang et al., IEEE 802.15.4J: Extend IEEE 802.15.4 Radio into the MBAN Spectrum, IEEE Wireless Communications, Oct. 2012, 2 pages.

* cited by examiner

WIRELESS MEDICAL BODY AREA NETWORK AND METHOD TO ASSOCIATE WIRELESS DEVICES THEREWITH

CROSS-REFERENCE TO RELATED APPLICATIONS

This application is a filing under 35 U.S.C. 371 of international application number PCT/US2015/050875, filed Sep. 18, 2015, which claims priority to GB application number 1423330.8, filed Dec. 30, 2014, the entire disclosures of each are hereby incorporated by reference.

TECHNICAL FIELD

The present disclosure relates to a wireless medical body area network, MBAN. More particularly, the present disclosure relates to a hub for a wireless MBAN, and a method of associating wireless devices with a wireless MBAN.

BACKGROUND

Traditionally medical devices, such as sensors, have been connected to each other, a host and/or a monitor through cables. A network of such devices applied to and around a single patient is called a medical body area network, MBAN. This MBAN can be used in a hospital or at home or any other suitable place. The devices included in and part of an MBAN can easily be seen by the connected cables. A new device can be connected to an existing MBAN by connecting the cable of the new device to a hub of the existing MBAN.

With wireless applications the communication can be carried out without a physical connection, such as a cable. An example of a wireless MBAN is disclosed in US 2009/0186577 A1. A wireless MBAN may give some advantages. However, it is difficult to wirelessly associate the devices to a specified host device (e.g. monitors or patient specific hub devices), because there are no cables to physically connect between the devices and the host. Typically the wireless device association is based on the serial number of the devices involved, or the device name, or the patient's identification. This is laborious and slow and requires extreme precision from the user to verify the serial number, device names, or patient identification. A single wrong digit will result in pairing and/or association failure. Human error and confusion is common in this situation and can lead to very serious consequences. When an association needs to be made it is normally preferred that it takes place quickly.

It is a problem to associate wireless devices to a wireless MBAN, especially for increasing the intuitiveness and speed of performing the association. It is a problem to find available and compatible devices and associate them in a simple manner and in an intuitive manner. Ease and intuitiveness and security are problems to consider. It is a problem to provide solutions that are economic and technically feasible, a solution must be possible and practical to perform in realty easily and conveniently, also in a medical environment. Medical environments inherently have strict regulations and health and safety aspects to consider.

SUMMARY OF THE INVENTION

The present disclosure is directed to a method of associating wireless devices with a wireless MBAN and a hub and wireless MBAN. This can be achieved by the features as defined by the independent claims. Further enhancements are characterized in the dependent claims. For this disclosure, medical devices, such as sensors, connected to each other and/or a host and/or a monitor through cables or wirelessly to a network applied to and around a single patient is called a medical body area network, MBAN. This MBAN can be used in a hospital or at home or any other suitable place.

According to one embodiment, a method of associating wireless devices with a wireless medical body area network, MBAN, where the wireless MBAN comprises at least one host, comprises the following: activating the host to search for wireless devices in range; displaying a list on the host of available wireless devices in range; selecting a wireless device on the list; and associating the selected wireless device on the list with the host.

According to one embodiment, displaying the list may comprise displaying each wireless device on the list with a unique representation on the list and the same unique representation on the wireless device itself. According to one embodiment, the unique representation may be one or a combination of the following: a color, a sequenced flash pattern, a sound, and a symbol. According to one embodiment, the unique representation may be an alphanumeric code.

According to one embodiment, only compatible wireless devices may be displayed on the list. According to one embodiment, the selected wireless device on the list may also be associated with any other wireless devices already connected to the host. According to one embodiment, the wireless device may be a sensor, for example a medical sensor.

According to one embodiment, a hub for a wireless medical body area network, MBAN, is configured as follows. The hub is configured as a host and, at least, configured to search for compatible wireless devices in range; display a list of available wireless devices in range; allow a selection of a wireless device on the list; and associate the wireless device on the list with the host.

According to one embodiment, the hub may be further configured to display each wireless device on the list with a unique representation in the list and to provide the same unique representation to each respective wireless device. According to one embodiment, the hub may be further configured to display the unique representation as one or a combination of the following: a color, a sequenced flash pattern, a sound, and a symbol. According to one embodiment, the hub may be configured to display the unique representation as an alphanumeric code.

According to one embodiment, the hub may be configured to only list compatible wireless devices. According to one embodiment, the hub may be configured to associate the wireless device with all other wireless devices already connected to the host.

According to one embodiment, a wireless medical body area network, MBAN, comprises wireless devices of which at least one wireless device is a hub, as disclosed above.

At least one embodiment provides a method of associating wireless devices with a wireless MBAN that allows starting the monitoring quickly and receiving real-time information on a patient's status enabling the caregivers to make clinical decisions and provide timely treatment for the patient. At least one embodiment provides an intuitive method to assist the association, pairing. At least one embodiment makes it easy to recognize and differentiate a wireless sensor from other similar sensors and enables creating a reliable association fast between a specified sensor and a host within a wireless MBAN. At least one embodiment provides the caregiver to have more time for the primary patient care tasks because the caregiver can quickly complete tasks related to operating the monitoring equipment. At least one embodiment provides an easy and intuitive method for associating wireless devices and also increases trustworthiness towards the whole system. These technical effects, as well as technical effects such as minimizing user workload and especially providing an easy and intuitive method for the association are highly evaluated within the industry.

At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

Figure 1:
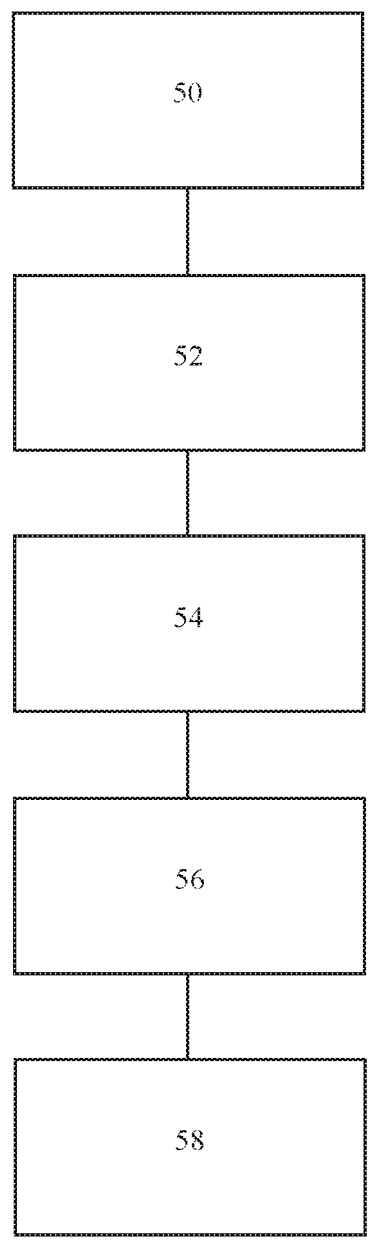
FIG. 1 shows a flow chart of a method according to an exemplary embodiment of the disclosure.
Figure 2:
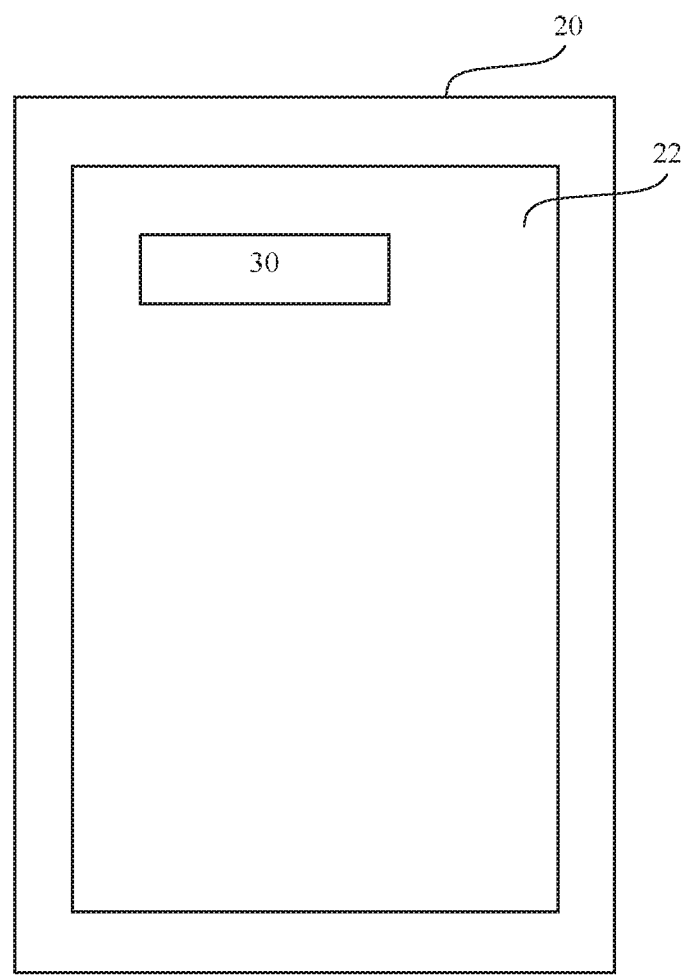
FIG. 2 is a diagrammatic illustration of a hub according to an exemplary embodiment of the disclosure.
Figure 3:
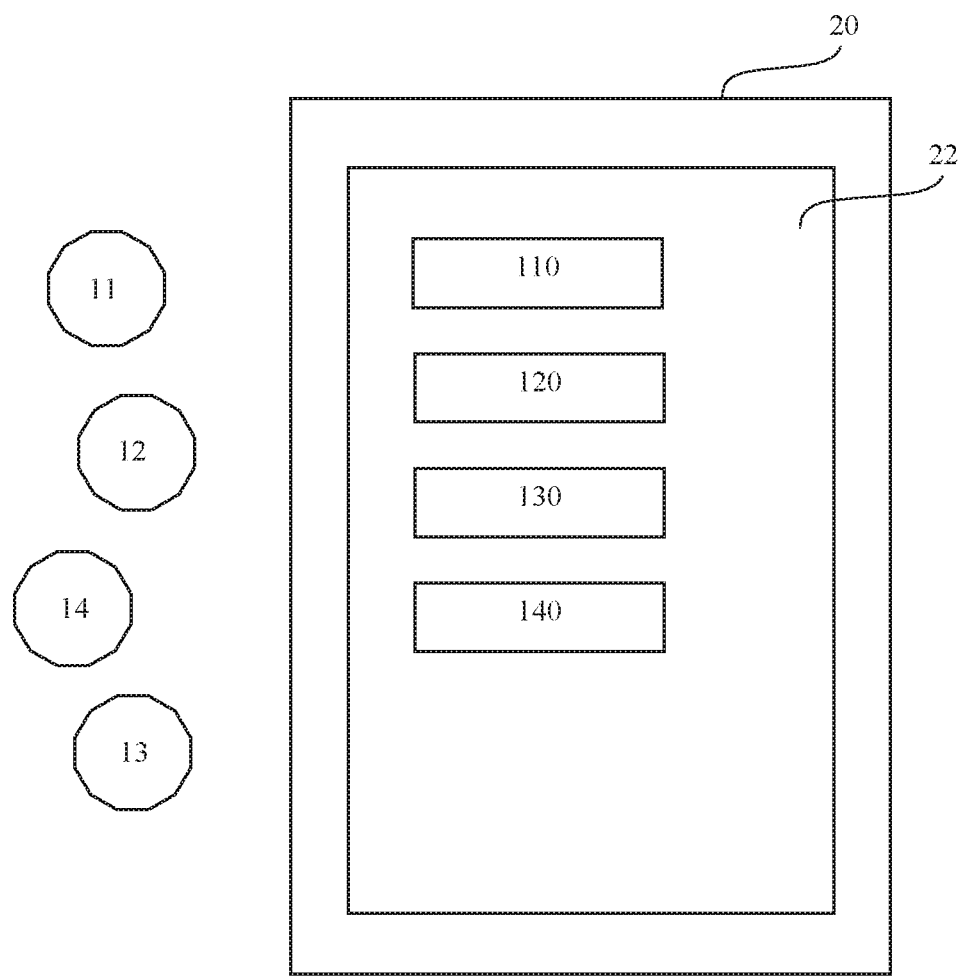
FIG. 3 is a diagrammatic illustration of a hub with a list according to an exemplary embodiment of the disclosure.

At least one embodiment makes use of active visual and/or auditory user interface, UI, indications produced on wireless devices within a wireless MBAN. A hub, a host device, may be activated to identify all available and compatible wireless sensor devices in an area its communication covers. The hub may communicate wirelessly or wired with a second network, for example an infrastructure of a hospital. Once the wireless sensor devices notice a host device searching for other wireless devices, for example sensors, they may identify themselves for example by displaying a unique representation, for example a color differentiating them from other found sensor devices. Each sensor may be represented on a display on the host by their colors. This enables a user to choose a sensor, identify it by the color and activate the connection. When associated to a host the sensor devices do not respond to other host devices searching for available sensors. In this way a user can associate wireless devices within a wireless MBAN in a simple, fast, and intuitive manner. For example, in a clinical environment tools are often used for monitoring a patient. To be able to start monitoring quickly and receiving real-time information on the patient's status enables the caregivers to make clinical decisions and provide timely treatment for the patient.

At least one embodiment provides an intuitive method of associating wireless devices with a wireless MBAN. The method makes it easy to recognize and differentiate a wireless device from other similar wireless devices and enables creating a reliable connection quickly between the specified wireless device and a host. Quickly completing tasks related to operating monitoring equipment frees the caregiver to have more time for primary patient care tasks. An easy and intuitive tool for the association also increases trustworthiness towards the whole wireless MBAN system. These technical effects make the disclosed embodiments highly desirable.

A wireless MBAN introduces user tasks relating to wireless devise association, which were not present in a traditional wired MBAN. Minimizing user workload for making an association is a valued technical effect by users. An easy and intuitive association, pairing, increases trustworthiness towards a wireless MBAN and the use thereof in the absence of cables or wires, and also adds to its appeal and generates a positive user experience. At least one embodiment introduces a more intuitive and easier method for the user to distinguish devices while performing the association task.

At least one embodiment may use visual and/or auditory indications to assist in creating the connection. Generating matching UI indications in both or all available and compatible wireless devices makes it easy to identify them and apply association. While the method and wireless MBAN may use, for example patient identification in a written form or NFC association, merging these methods with one or more of the disclosed embodiments increases the intuitiveness and speed of performing the association.

One embodiment discloses a method of associating wireless devices with a wireless medical body area network, MBAN. In this regard, please see FIGS. 1-4. An association may be pairing and/or a connection allowing for communication. The wireless MBAN comprises at least one host 20. The method may comprise as a first step 50 to activate the host 20 to search for wireless devices 11, 12, 13, 14 in range. This activation may be made by activating a command on the host, for example by selecting an association icon 30 on a screen 22 of the host 20. A second step 52 may be displaying a list 110, 120, 130, 140 on the host 20 of available wireless devices 11, 12, 13, 14 in range. A third step 54 may be selecting a wireless device 12, 120 on the list. This may be made by a user selecting one icon, a unique identification, on the list. A fourth step 56 may be associating the selected wireless device 12 on the list with the host 20. Hereby the wireless device 12 is set up to communicate with at least the host within the wireless MBAN.

According to one embodiment, displaying the list comprises displaying each wireless device 11, 12, 13, 14 on the list 110, 120, 130, 140 with a unique representation 110, 120, 130, 140 on the list and the same unique representation 11, 12, 13, 14 on the wireless device itself. According to one embodiment, the unique representation is one or a combination of the following: a color, a sequenced flash pattern, a sound, and a symbol. For example each wireless device 11, 12, 13, 14, for example medical sensors, may each display a unique color. The list 110, 120, 130, 140 on the host 20 may list each wireless device in the list with the corresponding color. In this way a user can quickly, easily and intuitive make an association and assure that the right sensor is associated. The technical effect hereof is that a fast and intuitive way of associating wireless devices to the wireless MBAN is achieved.

According to one embodiment, only compatible wireless devices are displayed on the list. In this way a user will easily note what devices can be connected, associated, within the wireless MBAN, and what devices can not be paired, associated, with the wireless MBAN.

According to one embodiment, a fifth step 58 may be that the selected wireless device 12 on the list is also associated with any other wireless devices already connected to the host. In this way further communication between devices within the wireless MBAN can be made because the selected wireless device 12 is not only associated with the hub of the wireless MBAN.

According to one embodiment, the wireless device is a sensor. The sensor is preferably a medical sensor for a wireless MBAN. The host 20 may communicate with a second network, such as the infrastructure of a hospital.

According to one embodiment, the unique representation may be an alphanumeric code. The alphanumeric code may be two or three or four or five characters long. It may be longer, but having an alphanumeric code of two or three or four or five characters allows for a fast, simple, and intuitive recognition for the association.

According to one embodiment, a hub for a wireless medical body area network, MBAN, is disclosed. See FIG. 2-4. The hub 20 may be configured as a host. Furthermore, the hub 20 may be configured to search for compatible wireless devices in range; configured to display a list 110, 120, 130, 140 of available wireless devices 11, 12, 13, 14 in range; configured to allow a selection of a wireless device on the list 110, 120, 130, 140; and configured to associate the wireless device on the list with the host.

According to one embodiment, the hub is further configured to display each wireless device 11, 12, 13, 14 on the list 110, 120, 130, 140 with a unique representation 110, 120, 130, 140 in the list and to provide the same unique representation to each respective wireless device 11, 12, 13, 14. According to one embodiment, the hub 20 may be further configured to display the unique representation as one or a combination of the following: a color, a sequenced flash pattern, a sound, and a symbol. The unique representation may be displayed on a display, a screen, of the wireless device 11, 12, 13, 14. The unique representation may be displayed on the screen 22 on the hub 20, for example as an icon with the unique representation. According to one embodiment, the hub 20 is configured to only list compatible wireless devices.

The host 20 can be configured so that when activated the host will search for all available wireless devices 11, 12, 13, 14, sensors, in its radio coverage area. The host 20 may then be so configured that when available and compatible wireless devices, sensors, notice the host searching, the wireless devices are identified by displaying a unique representation and the corresponding unique representation may also be displayed on the list of the host to identify the wireless device. The representation is unique in the sense that each representation is only used for one wireless device. For example if one wireless sensor is identified as being green on the wireless sensor itself, and listed as green in the list on the host, then no other wireless device use the same green color. The association, the pairing and connection of the wireless device 12 to the hub 20 of the wireless MBAN, may be made by selecting the wireless device 12, for example by clicking on its symbol 120 on the screen 22 of the host 20.

According to one embodiment, the hub 20 may be configured to associate the wireless device with all other wireless devices already connected to the host. Hereby each wireless devices in the wireless MBAN know all other wireless devices. This allows for efficient communication and management of the wireless MBAN.

According to one embodiment, the hub may further be configured to display the unique representation as an alphanumeric code. The alphanumeric code may be two or three or four of five characters long. It may be longer, but having an alphanumeric code of two or three or four or five characters allows for a fast, simple, and intuitive recognition for the association.

Figure 4:
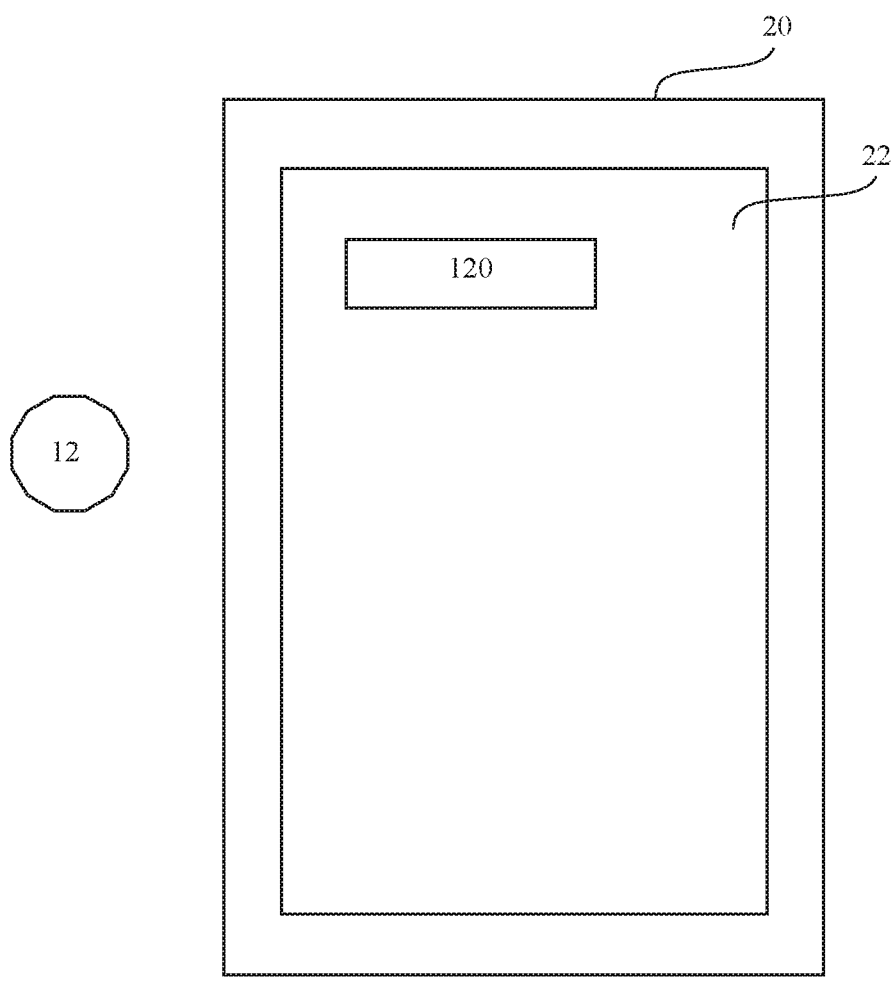
FIG. 4 is a diagrammatic illustration of an associated device and hub according to an exemplary embodiment of the disclosure.

According to one embodiment, a wireless MBAN comprises wireless devices of which at least one wireless device is a hub as described. The wireless MBAN may for example be as shown in FIG. 4 the host 20 and the wireless device 12. This example would be a wireless MBAN with only one sensor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of associating wireless devices with a wireless medical body area network (MBAN) that comprises at least one host, the method comprising:
   activating the host to search for wireless devices in range;
   displaying a list on the host of available wireless devices in range, wherein each wireless device is displayed on the list with a unique visual feature which is the same unique visual feature displayed on the respective wireless device itself;
   receiving selection of a wireless device on the list; and
   establishing communication between the selected wireless device on the list and the host.

2. The method according to claim 1, wherein the unique visual feature is one or a combination of the following: a color, a sequenced flash pattern, and a symbol.

3. The method according to claim 1, wherein only compatible wireless devices are displayed on the list.

4. The method according to claim 1, further comprising establishing communication between the selected wireless device on the list and any other wireless devices already connected to the host.

5. The method according to claim 1, wherein the wireless device is a sensor.

6. The method according to claim 1, wherein the unique visual feature is an alphanumeric code.

7. A hub for a wireless medical body area network (MBAN), the hub being configured as a host and, at least, configured to:
   search for compatible wireless devices in range;
   display a list of available wireless devices in range, wherein each wireless device is displayed on the list with a unique visual feature which is the same unique visual feature displayed on the respective wireless device itself;
   receive a selection of a wireless device on the list; and
   establish communication between the selected wireless device on the list and the host.

8. The hub according to claim 7, wherein the hub is further configured to display the unique visual feature as one or a combination of the following: a color, a sequenced flash pattern, and a symbol.

9. The hub according to claim 7, wherein the hub is configured to only list compatible wireless devices.

10. The hub according to claim 7, wherein the hub is configured to establish communication between the selected wireless device and all other wireless devices already connected to the host.

11. The hub according to claim 7, wherein the hub is further configured to display the unique visual feature as an alphanumeric code.

12. A wireless medical body area network (MBAN) comprising wireless devices of which at least one wireless device is a hub, the hub configured to:
  search for wireless devices in range;
  display a list of available wireless devices in range, wherein each wireless device is displayed on the list with a unique visual feature which is the same unique visual feature displayed on the respective wireless device itself;
  receive a selection of a wireless device on the list; and
  establish communication between the selected wireless device on the list and the hub.

13. The MBAN of claim 12, wherein the hub is further configured to display the unique visual feature as one or a combination of the following: a color, a sequenced flash pattern, and a symbol.

14. The MBAN of claim 12, wherein the hub is configured to only list compatible wireless devices.

15. The MBAN of claim 12, wherein the hub is configured to associate establish communication between the selected wireless device and all other wireless devices already connected to the hub.

16. The MBAN of claim 12, wherein the hub is further configured to display the unique visual feature as an alphanumeric code.

* * * * *